United States Patent [19]

Gignier et al.

[11] 4,174,449

[45] Nov. 13, 1979

[54] PROCESS FOR THE REDUCTION OF QUINIDINONE TO QUINIDINE

[76] Inventors: Jean P. Gignier, 4 Rue de Capucins; Jacques Bourrelly, 4 Ave. de Chateau, both of 92190, Meudom, France

[21] Appl. No.: 915,010

[22] Filed: Jun. 13, 1978

[51] Int. Cl.² ............................................ C07D 453/04
[52] U.S. Cl. ..................................................... 546/134
[58] Field of Search ............ 260/284, 288 CE, 448 A; 546/134

[56] References Cited

U.S. PATENT DOCUMENTS

| | | | |
|---|---|---|---|
| 3,696,047 | 10/1972 | Nelson | 252/188 |
| 3,753,992 | 8/1973 | Gutzwiller et al. | 260/284 |
| 3,907,806 | 9/1975 | Grethe et al. | 260/284 |
| 3,989,691 | 11/1976 | Taylor et al. | 260/240 R |
| 4,093,619 | 6/1978 | Jarreau et al. | 260/284 |

FOREIGN PATENT DOCUMENTS

| | | | |
|---|---|---|---|
| 877611 | 5/1953 | Fed. Rep. of Germany | 260/284 |
| 883154 | 7/1953 | Fed. Rep. of Germany | 260/284 |

OTHER PUBLICATIONS

Grethe, et al., J. Am. Chem. Soc., vol. 93, No. 22, 5904–5907 (1971).
Woodward, et al., J. Am. Chem. Soc., vol. 67, 1425–1429 (1945).
Doering, et al., J. Am. Chem. Soc., vol. 69, 1700–1710 (1947).

*Primary Examiner*—Donald G. Daus
*Assistant Examiner*—Diana G. Rivers
*Attorney, Agent, or Firm*—Thomas R. Boland

[57] ABSTRACT

Quinidinone is reduced to quinidine through reaction with a reducing agent, selected from aklyl-substituted aluminum hydrides or alkali metal alkyl-substituted aluminum hydrides, in the presence of a stereospecific orienting agent, such as pyridine.

18 Claims, No Drawings

PROCESS FOR THE REDUCTION OF QUINIDINONE TO QUINIDINE

BACKGROUND OF THE INVENTION

This invention relates to a process for the stereospecific reduction of quinidinone to quinidine.

Quinidine is a dextrorotatory stereoisomer of quinine which is pharmacologically useful as an antiarrhythmic in treating heart irregularities. It is found naturally in cinchona bark but only in amounts up to 3% so that its commercial exploitation has required alternate means of supply. Such means have commonly involved variations of the Oppenhauer oxidation and Meerwein-Ponndorff reduction reactions (see for example, German Pat. Nos. 833,154 and 877,611), but in each instance, the known reactions produce four principal reaction products—quinine and its $C_9$ epimer, epiquinine, quinidine and its $C_9$ epimer, epiquinidine, as well as the intermediates of the $C_9$ ketone form, quininone and quinidinone, all of which are in equilibrium in solution passing through a common transitory state. When such epibases are present, even in small amounts, they significantly slow crystallization of quinine and quinidine from saturated solutions, and thus lower the yields of such substances. In addition, it has been demonstrated that such epi-bases cannot be recycled like quinine under the conditions of the reaction. Indeed, a mixture of quinine and epiquinine will not give the same equilibrium, all other conditions being the same, as a quantity of pure quinine. Consequently, considerable effort has been given to solving the problem of how to influence the equilibrium toward the formation of the desired product, i.e. quinidine, while entirely avoiding the formation of epiquinine and epiquinidine. Nevertheless, the best of such efforts have established coefficients of transformation which are not much lower than 1.20 to 1.25 kilograms of anhydrous quinine base used per kilogram of anhydrous quinidine base isolated, and required the recycling of about 40% to 50% of the quinine used in the synthesis. Of course, such recycling processes generate considerably higher production costs, since they include treating the mother liquors, separating unreactive quinine and purifying it before returning it to the reaction. In some cases, because of these higher costs, it has proven to be more economical to follow a quantitative synthesis without recycling of the starting material.

Recently, attempts have been made to utilize certain aluminum hydrides in the total synthesis of a series of alkaloids belonging to the quinine and quinidine family. In particular, the reduction of quinidinone to quinidine using diisobutylaluminum hydride in toluene has been described (see Grethe, et al., J. Am. Chem. Soc. 93, 5904 (1971)). However, these methods have not solved the problems resulting from the presence of unwanted by-products since, besides quinidine, such by-products as quinine and the epi-bases are produced by such methods in unacceptable amounts; for example, 35% of such by-products were produced in the process described in the above-mentioned reference. Furthermore, such by-products are found in equal proportions, a situation which is incompatible with economical production.

SUMMARY OF THE INVENTION

This invention provides an essentially quantitative process for reducing quinidinone to quinidine but avoids formation of undesirable by-products including quinine, epiquinine and epiquinidine. The process comprises reacting quinidinone with a reducing agent selected from the group consisting of an alkyl-substituted aluminum hydride and an alkali metal alkyl-substituted aluminum hydride in the presence of a stereospecific orienting agent which is an organic base including a nitrogen-containing heterocyclic ring, such as, for example, pyridine, pyrrole, alkyl-substituted pyridine, or alkyl-substituted pyrrole. Preferably, the quinidinone, reducing agent and orienting agent are dissolved in an inert aromatic hydrocarbon solvent, such as benzene, or in an inert ether such as dioxan.

DESCRIPTION OF THE PREFERRED EMBODIMENTS

The reduction of quinidinone to quinidine according to this invention may be exemplified by the following reaction scheme:

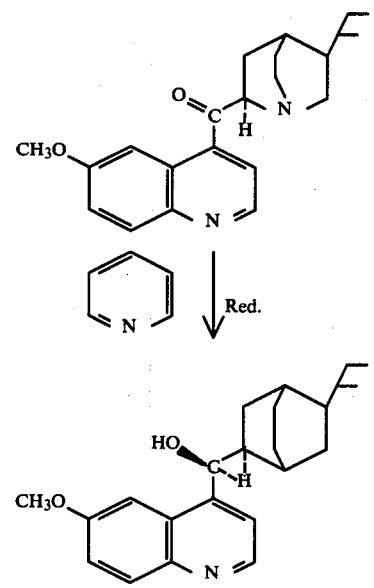

The reduction is achieved by reacting quinidinone with a reducing agent selected from an alkyl-substituted aluminum hydride, such as diisobutyl aluminum hydride, or an alkali metal alkyl-substituted aluminum hydride, such as sodium diethylaluminum hydride.

The orienting agent is selected from the group consisting of pyridine, alkyl-substituted pyridine, pyrrole, and alkyl-substituted pyrrole. Usually, the orienting agent is present in the reaction mixture in a concentration of at least about 0.5% by weight.

Preferably, the reaction is carried out in an inert solvent selected from the group consisting of aromatic hydrocarbon solvents such as benzene, toluene and xylene, ethers, e.g., tetrahydrofuran, dioxan, or dialkyl ethers such as dibutyl ether, and mixtures thereof.

Also, in a preferred embodiment the reaction will be carried out at a temperature no greater than room temperature; most preferably not higher than 15° C.

The reaction proceeds in a completely stereospecific manner yielding a reaction product substantially free of by-products or impurities, i.e. less than 5% by weight.

The following examples will further illustrate the invention, and unless otherwise indicated all amounts or proportions will be by weight.

EXAMPLE I 500 ml. of tetrahydrofuran, 100 g. of crystallized quinidinone, and 25 ml. of anhydrous pyridine are mixed in a dry, nitrogen blanketed reactor. A 25% solution of diisobutylaluminum hydride in toluene is prepared and 250 ml. are introduced in the reactor, the temperature being kept below 15° C. by cooling, and the progress of the reaction is monitored by thin layer chromatography. After the reduction is completed, the mixture is subjected to fractional distillation under vacuum (25 mm Hg absolute) in order to eliminate the THF overhead with a minimum quantity of toluene. After cooling, the aluminum complex is decomposed by adding water slightly in excess of the stoichiometric quantity. The solids are filtered and extracted by toluene at 80° C. The 96 g. of raw quinidine base obtained from the toluene solution exhibited a melting point of 173° C. and $\alpha_D$ (1.5% in ethanol)=256°.

EXAMPLE II 600 ml. anhydrous pyridine, 100 g. crystallized quinidinone, and 300 ml. 25% solution of diisobutylaluminum hydride (DIBAH) in toluene were in a reaction vessel and the reaction was allowed to proceed until the reduction was completed as indicated by thin layer chromatography. The mixture was then heated under vacuum (25 mm Hg) to remove the pyridine. The reaction mixture was then treated with 750 ml. of a 50/50 mixture of water and ethanol, and after refluxing for 2 hours and cooling, 92.7 g. of quinidine base were obtained, exhibiting a melting point of 174.5° C.

EXAMPLE III 300 ml. tetrahydrofuran, 250 ml. anhydrous pyridine, and 100 g. crystallized quinidinone were mixed in a reactor, followed by 250 ml. of a 25% solution of diisobutylaluminum hydride (DIBAH) in toluene. Otherwise the same procedure was followed as in Example I. The reaction produced a yield of 94.5 g. of quinidine having a melting point of 174° C.

The quinidinone utilized in the invention may be prepared by any known method. However, it is preferred for economical reasons that the quinidinone be synthesized according to the process described in the U.S. patent application filed concurrently by the present inventors entitled "Process For Preparing Quininones" Ser. No. 915,009, which disclosure is incorporated herein by reference. That is to say, quinidinone is prepared by reacting an amino secondary alcohol with an alkali metal ketyl in an inert solvent to produce a mixture of quininone and quinidinone from which substantially pure quinidinone may be crystallized.

This invention may be embodied in specific forms other than those described without departing from the spirit or the essential characteristics of the invention. Therefore, the present embodiments are to be considered in all respects as illustrative and not restrictive, the scope of the invention being indicated by the appended claims rather than by the foregoing description. Thus, all changes which come within the meaning and range of equivalency of the claims are intended to be embraced within those claims.

What is claimed is:

1. A process for reducing quinidinone to quinidine comprising reacting quinidinone with a reducing agent selected from the group consisting of alkyl-substituted aluminum hydrides, and alkali metal alkyl-substituted aluminum hydrides in the presence of an orienting agent selected from the group consisting of pyridine, alkyl-substituted pyridine, pyrrole, and alkyl-substituted pyrrole.

2. A process according to claim 1 wherein said reducing agent is selected from the group consisting of diisobutylaluminum hydride and sodium diethylaluminum hydride.

3. A process according to claim 1 wherein the reduction is carried out with a reaction mixture including quinidinone, the reducing agent, and the orienting agent dissolved in an inert solvent.

4. A process according to claim 3 wherein said inert solvent is selected from the group consisting of aromatic hydrocarbon solvents, ethers, and mixtures thereof.

5. A process according to claim 4 wherein said aromatic hydrocarbon solvent is selected from the group consisting of benzene, toluene, and xylene.

6. A process according to claim 4 wherein said ether is selected from the group consisting of tetrahydrofuran, dioxan, and dibutyl ether.

7. A process according to claim 1, wherein the reaction is carried out in the presence of pyridine or mixtures of pyridine with an ether.

8. A process according to claim 7, wherein said ether is a dialkyl ether.

9. A process according to claim 7, wherein said ether is selected from the group consisting of tetrahydrofuran and dioxan.

10. A process according to claim 1, wherein the reaction is carried out at temperatures no greater than room temperature.

11. A process according to claim 10 wherein the reaction is carried out at temperatures no greater than 15° C.

12. A process according to claim 7 wherein the orienting agent is pyridine which is present in a concentration of at least 0.5% by weight.

13. A process for reducing quinidinone to quinidine comprising reacting quinidinone with a reducing agent selected from the group consisting of diisobutylaluminum hydride and sodium diethylaluminum hydride in the presence of pyridine and in an inert solvent selected from the group consisting of aromatic hydrocarbon solvents, ethers, and mixtures thereof.

14. A process according to claim 13 wherein said aromatic hydrocarbon solvent is selected from the group consisting of benzene, toluene and xylene.

15. A process according to claim 13 wherein said ether is selected from the group consisting of tetrahydrofuran, dioxan, and dibutyl ether.

16. A process according to claims 1 or 13 wherein said quinidinone is produced by the oxidation of an amino secondary alcohol selected from the group consisting of quinine, epiquinine, quinidine, epiquinidine and mixtures thereof, by reacting said alcohol with a metal ketyl, which is the reaction product of an alkali metal and diphenyl ketone, in an inert hydrocarbon solvent.

17. A process according to claim 16 wherein said alkali metal is selected from sodium, potassium and lithium and said diphenyl ketone is selected from benzophenone and fluorenone.

18. A process according to claim 17 wherein said solvent is selected from the group consisting of benzene, toluene and xylene.

* * * * *